United States Patent [19] [11] 4,112,002
Schneider et al. [45] Sep. 5, 1978

[54] MONONITROTRIFLUOROMETHYL DIPHENYLETHERS

[75] Inventors: Louis Schneider, Elizabeth; David E. Graham, Westfield, both of N.J.

[73] Assignee: GAF Corporation, New York, N.Y.

[21] Appl. No.: 760,952

[22] Filed: Jan. 21, 1977

[51] Int. Cl.² .............................................. C07C 43/28
[52] U.S. Cl. ............................ 260/612 R; 260/613 R; 424/340; 424/341; 71/124
[58] Field of Search ........................ 260/612 R, 613 R

[56] References Cited
U.S. PATENT DOCUMENTS

| | | | |
|---|---|---|---|
| 3,420,892 | 1/1969 | Martin et al. | 260/612 R |
| 3,647,888 | 3/1972 | Rohr et al. | 260/612 R |
| 3,776,961 | 12/1973 | Theissen | 260/613 R |

Primary Examiner—Bernard Helfin
Attorney, Agent, or Firm—Walter C. Kehm; Walter Katz

[57] ABSTRACT

Mononitrotrifluoromethyl diphenylethers having the formula:

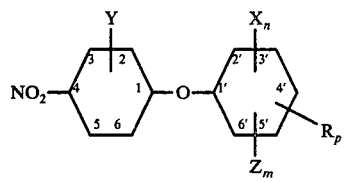

where Y is $CF_3$ substituted at the 2- or 3- position,
X is halogen,
n is 0,1,2 or 3,
Z is lower alkyl,
m is 0 or 1,
R is lower alkoxy, and
p is 0 or 1, are prepared by reacting a chloronitrotrifluoromethylbenzene with a phenolate.

The compounds of the invention show good fungicidal and post-emergence herbicidal activity.

2 Claims, No Drawings

MONONITROTRIFLUOROMETHYL DIPHENYLETHERS

BACKGROUND OF THE INVENTION

1. Field of the Invention

This invention relates to agricultural chemicals, and more particularly to substituted-diphenylethers which exhibit good fungicidal and herbicidal activity.

2. Description of the Prior Art

Diphenylethers compounds are known in the art as being useful agricultural chemicals. Accordingly, it is the object of this invention to provide new and improved substituted-diphenylethers which exhibit good fungicidal and herbicidal activity.

SUMMARY OF THE INVENTION

The present invention provides mononitrotrifluoromethyldiphenylethers having the formula:

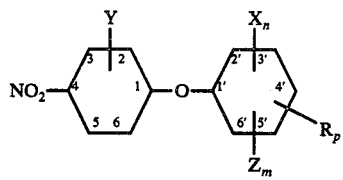

where Y is $CF_3$ substituted at the
2- or 3- position,
X is halogen,
n is 0,1,2 or 3,
Z is lower alkyl,
m is 0 or 1,
R is lower alkoxy, and
p is 0 or 1, where
Y is $CF_3$ substituted at the 2- or 3-position,
X is halogen,
n is 0, 1, 2 or 3,
Z is lower alkyl,
m is 0 or 1,
R is lower alkoxy, and
p is 0 or 1,
are prepared by reacting a chloronitrotrifluoromethylbenzene with a phenolate.

The compounds of the invention shows good fungicidal activity against bean mildew and bean rust, and post-emergence herbicidal activity against foxtail millet, crabgrass and pigweed in herbicidal tests.

DESCRIPTION OF THE PREFERRED EMBODIMENTS

The compounds of the invention are prepared by a condensation reaction between a chloromononitrotrifluoromethylbenzene and a phenolate. The chloromononitrotrifluoromethylbenzene is obtained by nitrating commercially available p-chlorotrifluoromethyl benzenes with a nitric-sulfuric acid mixture containing oleum, in the conventional manner. The phenolate is prepared from the corresponding phenol and potassium carbonate. The condensation reaction is effected in dimethylformamide solvent at about 100° C for five hours. The solvent then is distilled off and the product crystallized from the filtrate.

The compounds of the invention are useful as agricultural fungicides when applied to the soil at the rate of about 1 to 25 lbs. per acre or as a foliar spray at concentration of about 31 to 260 ppm. They show foliar fungicidal activity against the following pathogens: bean mildew and bean rust, and post-emergence hebicidal activity against foxtail millet, crabgrass and pigweed in herbicidal tests.

The materials of the present invention may be applied to those fungus susceptible plants on site at a rate of about 1 or less to about 25 pounds per acre depending on various circumstances of the susceptibility to the fungus, the weather, the stage of growth and various other factors. The material may be applied as a dust or spray. As a dust it is more practical to extend it with diluents such as bentonite, chalk, clay, diatomaceous earth, fullers earth, mica, ground slate or any of the other usual carriers for agricultural chemicals. As a spray it may be incorporated into water as a solution. The higher molecular weight compounds may be dissolved first in a solvent, such as an alcohol, or a petroleum fraction, such as isoparaffinic hydrocarbons, naphtha or kerosene, which may be dissolved in a suitable solvent and fogged or sprayed without water. Usually it is desirable to incorporate emulsifying agents and other wetting agents to insure complete contact with the fungus.

Following are examples of preparation of the compounds of the invention, and are presented by way of illustration and are not intended to be limiting unless otherwise specified.

EXAMPLE 1

The compounds listed in Table I are prepared by first forming a phenolate by reacting 0.063 mole of the appropriate phenol and 0.065 mole of potassium carbonate in 100 ml of dimethylformamide under a nitrogen blanket in a 250cc 4-necked flask equipped with stirrer, thermometer, and condenser for 2 hours at 145°–150° C. The dimethylformamide then is removed by distillation at atmospheric pressure to a temperature of 155°–160° C and finally under 30 mm vacuum. Fresh dimethylformamide (100 ml) and 0.05 mole of the appropriate chloronitrotrifluoromethylbenzene then are added to the phenolate and heated for 5 hours at 100° C. The dimethylformamide is removed under 5 mm vacuum and 45 ml of methanol is added. The solid potassium chloride formed during the condensation then is filtered from the hot methanolic solution, and the desired product is crystallized from the filtrate at 0.5° C.

TABLE I

| Compound | Phenol | Trifluoromethylbenzene | Yield (%) | M.P. (° C) | % Nitrogen Calc. | found | % Chlorine Calc. | found |
|---|---|---|---|---|---|---|---|---|
| 1 | 4-chloro | 5-chloro-2-nitro | 57 | 63–64 | 4.40 | 4.20 | 11.16 | 11.33 |
| 2 | 2,4-dichloro | 5-chloro-2-nitro | 82 | 59–61 | 3.98 | 3.86 | 20.13 | 20.27 |
| 3 | 2,6-dichloro | 5-chloro-2-nitro | 68 | 103–104 | 3.98 | 4.07 | 20.13 | 20.42 |
| 4 | 2-chloro-5-methoxy | 5-chloro-2-nitro | 75 | 67–68 | 4.02 | 3.26 | 10.19 | 10.96 |
| 5 | 4-methyl | 5-chloro-2-nitro | 37 | 55–57 | 4.71 | 4.69 | — | — |
| 6 | 4-chloro | 2-chloro-5-nitro | 69 | 74–76 | 4.40 | 4.37 | 11.16 | 11.47 |
| 7 | 2,6-dichloro | 2-chloro-5-nitro | 80 | 94–96 | 3.98 | 4.46 | 20.13 | 20.68 |
| 8 | 2,4,5-trichloro | 2-chloro-5-nitro | 67 | 98–99 | 3.62 | 3.52 | 27.52 | 27.94 |
| 9 | 2-chloro-5-methoxy | 2-chloro-5-nitro | 35 | 80–81 | 4.02 | 3.95 | 10.19 | 10.17 |

TABLE I-continued

| Compound | Phenol | Trifluoromethylbenzene | Yield (%) | M.P. (° C) | % Nitrogen Calc. | % Nitrogen found | % Chlorine Calc. | % Chlorine found |
|---|---|---|---|---|---|---|---|---|
| 10 | 4-fluoro | 2-chloro-5-nitro | 53 | 37–39 | 4.65 | 4.49 | — | — |

EXAMPLE 2

Foliar Fungicide Tests

Compound 1 was tested on bean powdery mildew as follows: Healthy young bean plants with fully expanded primary leaves in 2½ inch pots were placed for 2 days on a greenhouse bench between two rows of infected plants covered with a mass of white, powdery conidia so that they were exposed to a shower of conidia.

The primary test plants with incipient infection were atomized while rotating on a turntable with a suspension of 250 ppm of a test material. The treated plants were then returned to the greenhouse bench near infected plants. After 7 days preliminary observations were made on the eradication of established infection present on the primary leaves at the time of spraying. The plants were reexamined 7 days later for infection on new growth as well as on the primary leaves to determine residual and systemic effects on the fungus. On both dates the leaves were rated on a scale of 0 (no suppression) to 10 (complete eradication or prevention of infection), and compared to the commercial standard Karathane, 2,4-dinitro-6-octylphenylcrotonate.

| Conc., ppm. | Fungitoxicity Rating Compound 1 | Fungitoxicity Rating Karathane |
|---|---|---|
| 250 | 9.0 | 10 |

EXAMPLE 3

Compound 4 was tested on bean rust as follows: Pinto beans grown in 2.5 inch pots for 9 to 12 days is sprayed while plants are rotating on a turntable with 100 ml. of a formulation at 125, 63 and 31 ppm. After the spray deposit dries, plants are placed in a moist chamber at 70° F. for 24 hours. After 7 to 9 days the severity of pustule formation is rated as in Example 2 and compared with the commercial standard Plantvax, 2,3-dihydro-5-carbanilido-6-methyl-1,4-oxathiin-4,4-dioxide.

| Conc., ppm. | Fungitoxicity Rating Compound 4 | Fungitoxicity Rating Plantvax |
|---|---|---|
| 125 | 8 | 10 |
| 63 | 8 | 10 |
| 31 | 7 | 9 |

EXAMPLE 4

Herbicidal Tests

Primary tests on Compounds 2 and 5 in Table I were made on two flats seeded with six species of representative monocotyledonous and dicotyledonous plants (foxtail millet, crabgrass and pigweed). The test chemical was applied to one such flat immediately after it was seeded. The other flat contained plants on which the first true leaves had developed. Both of these flats were sprayed, simultaneously, with the test chemical at 2080 ppm, a rate sufficient to give 10 lb/acre (104 mg in 50 ml of water on 144 square inches). Diuron, 3-(3,4-dichlorophenyl)-1,1-dimethylurea as a standard was applied post-emergence at rate of 2.5, lb/acre. The response was rated 12 to 21 days after treatment on a scale of 0 to 10 where 0 represents no injury and 10 represents complete kill.

| Test Plant | Post-Emergence Herbicidal Rating Compound 2 | Post-Emergence Herbicidal Rating Compound 5 | Standard (Divron) |
|---|---|---|---|
| Foxtail Millet | 9 | 10 | 10 |
| Crabgrass | 8 | 7 | 10 |
| Pigweed | 10 | 10 | 10 |

While the invention has been described with particular reference to certain embodiments thereof, it will be understood that certain modifications and changes may be made which are within the skill of the art. Therefore it is intended to be bound only by the appended claims.

What is claimed is:

1. A compound having the formula:

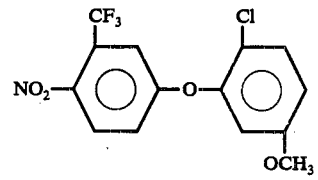

2. A compound having the formula:

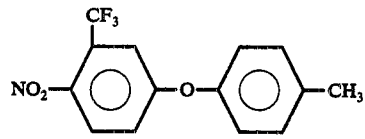

* * * * *